(12) United States Patent
Termanini et al.

(10) Patent No.: US 12,121,373 B2
(45) Date of Patent: Oct. 22, 2024

(54) SURGICAL TRAYS, INSTRUMENTS AND METHODS FOR IMPLANTING A HIP REPLACEMENT PROSTHESIS

(71) Applicant: HIP INNOVATION TECHNOLOGY, LLC., Boca Raton, FL (US)

(72) Inventors: Zafer Termanini, Port Saint Lucie, FL (US); Steven MacDonald, London (CA); Brian Vanhiel, Smyrna, GA (US); Taylor Davis, Atlanta, GA (US)

(73) Assignee: HIP INNOVATION TECHNOLOGY, LLC., Boca Raton, FL (US)

( * ) Notice: Subject to any disclaimer, the term of this patent is extended or adjusted under 35 U.S.C. 154(b) by 0 days.

(21) Appl. No.: 16/826,809

(22) Filed: Mar. 23, 2020

(65) Prior Publication Data
US 2020/0222141 A1    Jul. 16, 2020

Related U.S. Application Data

(62) Division of application No. 15/746,304, filed as application No. PCT/US2016/047031 on Aug. 15, 2016.
(Continued)

(51) Int. Cl.
*A61B 50/33* (2016.01)
*A61B 17/00* (2006.01)
(Continued)

(52) U.S. Cl.
CPC .............. *A61B 50/33* (2016.02); *A61B 50/20* (2016.02); *A61B 50/30* (2016.02); *A61B 50/34* (2016.02); *A61F 2/0095* (2013.01); *A61F 2/34* (2013.01); *A61F 2/36* (2013.01); *A61F 2/3609* (2013.01); *A61F 2/4637* (2013.01); *A61F 2/4684* (2013.01); *A61B 2017/00446* (2013.01);
(Continued)

(58) Field of Classification Search
CPC ......... A61B 50/33; A61B 50/20; A61B 50/22; A61F 2/34; A61F 2002/344
USPC ........................................................ 206/370
See application file for complete search history.

(56) References Cited

U.S. PATENT DOCUMENTS 4,206,517 A    6/1980  Pappas et al.
5,080,677 A    1/1992  Shelley
(Continued)

FOREIGN PATENT DOCUMENTS

AU    2006200078 B2    7/2006
EP       2668930 A1   12/2013
(Continued)

OTHER PUBLICATIONS

International Search Report for corresponding application PCT/US2016/047031 dated Jan. 12, 2017.
(Continued)

*Primary Examiner* — Anthony D Stashick
*Assistant Examiner* — Raven Collins
(74) *Attorney, Agent, or Firm* — Norris McLaughlin PA

(57) ABSTRACT

Surgical trays, tools and methods for use in hip replacement surgery wherein the hip replacement prosthesis is a reverse hip prosthesis. The trial components, specialized tools and methods of the invention enable a surgeon to identify the optimum components of the reverse hip prosthesis for implantation in a patient based on the sizes and angles best adapted to the patent's anatomy.

15 Claims, 19 Drawing Sheets

Related U.S. Application Data

(60) Provisional application No. 62/208,127, filed on Aug. 21, 2015.

(51) Int. Cl.

| | | |
|---|---|---|
| *A61B 17/16* | (2006.01) | |
| *A61B 17/17* | (2006.01) | |
| *A61B 50/20* | (2016.01) | |
| *A61B 50/30* | (2016.01) | |
| *A61B 50/34* | (2016.01) | |
| *A61F 2/00* | (2006.01) | |
| *A61F 2/34* | (2006.01) | |
| *A61F 2/36* | (2006.01) | |
| *A61F 2/46* | (2006.01) | |
| *A61F 2/30* | (2006.01) | |

(52) U.S. Cl.
CPC .. *A61B 2017/00451* (2013.01); *A61B 17/1615* (2013.01); *A61B 17/1655* (2013.01); *A61B 17/1659* (2013.01); *A61B 17/17* (2013.01); *A61B 2050/3007* (2016.02); *A61B 2050/3008* (2016.02); *A61F 2002/30331* (2013.01); *A61F 2002/30332* (2013.01); *A61F 2002/30405* (2013.01); *A61F 2002/30784* (2013.01); *A61F 2002/3483* (2013.01); *A61F 2002/3615* (2013.01); *A61F 2002/4622* (2013.01); *A61F 2002/4629* (2013.01); *A61F 2002/4638* (2013.01); *A61F 2002/4641* (2013.01)

(56) References Cited

U.S. PATENT DOCUMENTS

| | | | |
|---|---|---|---|
| 5,122,145 A * | 6/1992 | Fishbane | A61B 17/6425 606/102 |
| 5,133,764 A | 7/1992 | Pappas et al. | |
| 5,156,626 A * | 10/1992 | Broderick | A61F 2/4684 623/22.12 |
| 5,284,483 A | 2/1994 | Johnson et al. | |
| 5,674,225 A | 10/1997 | Mueller | |
| 5,824,078 A | 10/1998 | Nelson et al. | |
| 5,824,483 A | 10/1998 | Houston, Jr et al. | |
| 5,879,401 A | 3/1999 | Besemer et al. | |
| 5,954,727 A | 9/1999 | Collazo et al. | |
| 6,395,004 B1 | 5/2002 | Dye et al. | |
| 6,565,575 B2 | 5/2003 | Lewis | |
| 6,991,656 B2 | 1/2006 | Mears | |
| 7,785,331 B2 | 8/2010 | Eisinger et al. | |
| 8,262,667 B1 | 9/2012 | Silver et al. | |
| 8,313,531 B2 | 11/2012 | Termanini | |
| 8,540,779 B2 | 9/2013 | Termanini | |
| 8,992,627 B2 * | 3/2015 | Termanini | A61F 2/3609 623/22.15 |
| 10,245,149 B2 | 4/2019 | Loffredo | |
| 2002/0025358 A1 | 2/2002 | Nelson et al. | |
| 2002/0193797 A1 | 12/2002 | Johnson et al. | |
| 2003/0163203 A1 * | 8/2003 | Nycz | A61F 2/30744 623/22.36 |
| 2005/0004680 A1 | 1/2005 | Saladino et al. | |
| 2006/0173548 A1 * | 8/2006 | Auxepaules | A61F 2/4684 623/22.15 |
| 2007/0219562 A1 | 9/2007 | Slone et al. | |
| 2007/0260256 A1 * | 11/2007 | Beaule | A61B 90/06 606/80 |
| 2008/0195106 A1 * | 8/2008 | Sidebotham | A61B 17/1617 606/80 |
| 2009/0048682 A1 | 2/2009 | Choi et al. | |
| 2009/0099665 A1 | 4/2009 | Taylor et al. | |
| 2011/0109035 A1 | 5/2011 | Spence et al. | |
| 2011/0186456 A1 * | 8/2011 | Bertazzoni | A61B 17/154 206/438 |
| 2011/0189635 A1 | 8/2011 | Lauridsen et al. | |
| 2011/0213373 A1 | 9/2011 | Fitz et al. | |
| 2011/0218563 A1 | 9/2011 | Termanini | |
| 2011/0218637 A1 | 9/2011 | Termanini | |
| 2011/0218638 A1 | 9/2011 | Termanini et al. | |
| 2012/0059383 A1 | 3/2012 | Murphy et al. | |
| 2012/0157887 A1 * | 6/2012 | Fanson | A61B 90/39 600/595 |
| 2012/0259338 A1 | 10/2012 | Carr et al. | |
| 2012/0271425 A1 | 10/2012 | Maurer | |
| 2013/0226183 A1 | 8/2013 | Xie et al. | |
| 2013/0345823 A1 | 12/2013 | Termanini et al. | |
| 2014/0012264 A1 | 1/2014 | Prybyla et al. | |
| 2014/0069841 A1 | 3/2014 | Pizzato et al. | |
| 2014/0128982 A1 | 5/2014 | Termanini | |
| 2014/0128987 A1 * | 5/2014 | Kelley | A61F 2/32 623/22.12 |
| 2014/0156011 A1 * | 6/2014 | Termanini | A61F 2/3609 623/19.12 |
| 2014/0200675 A1 | 7/2014 | Termanini | |
| 2015/0010440 A1 | 1/2015 | Roudebush et al. | |
| 2015/0076023 A1 | 3/2015 | Kinyon | |
| 2015/0173906 A1 | 6/2015 | Winslow et al. | |
| 2016/0249996 A1 * | 9/2016 | Gerstner | F16M 11/10 211/130.1 |
| 2016/0347370 A1 | 12/2016 | Koga et al. | |
| 2017/0035571 A1 * | 2/2017 | Loffredo | A61F 2/3609 |
| 2018/0168821 A1 * | 6/2018 | Termanini | A61F 2/4609 |
| 2018/0193168 A1 * | 7/2018 | Termanini | A61F 2/32 |
| 2018/0318089 A1 | 11/2018 | Carr et al. | |

FOREIGN PATENT DOCUMENTS

| | | |
|---|---|---|
| JP | H08510945 A | 11/1996 |
| JP | 2009530021 A | 8/2009 |
| JP | 3165299 U | 1/2011 |
| JP | 2013521864 A | 6/2013 |
| JP | 2015529463 A | 11/2014 |
| JP | 2015504719 A | 2/2015 |
| JP | 2018523521 A | 8/2018 |
| WO | 2011005191 A2 | 1/2011 |
| WO | 2011112353 A1 | 9/2011 |
| WO | 2013025308 A1 | 2/2013 |
| WO | 2013032589 A1 | 3/2013 |
| WO | 2015044680 A1 | 4/2015 |
| WO | 2017019329 A1 | 2/2017 |

OTHER PUBLICATIONS

Written Opinion of the International Searching Authority for corresponding application PCT/US2016/047031 dated Jan. 12, 2017.
J.A. Pachore, et al., "My Trolley for Total Hip Arthroplasty", in Basics in Hip and Knee Arthroplasty by Shrinand Vaidya; May 10, 2015, Elsevier India; 1st Edition; Chapter 32, pp. 367-373.
EP Office Action in corrresponding application EP 16839186.2 dated Mar. 17, 2020.
Pachore, J.A., et al.,:"Basics in Hip Arthroplasty", Elsevier India, 1st Edition, ch. 32, pp. 367-373, 2015.
EPO Office Action in corresponding application 16839815.4 dated Oct. 9, 2019.
Supplemental Partial Search European Report for corresponding application EP 16839815 dated Apr. 26, 2019.
Unknown, "Kyocera PerFix JMM Hip System", Japan Medical Materials, pp. 1-20.
Unknown, "M.B.T. Revision Tray", DePuy, pp. 1-38.
PCT Written Opinion of the International Searching Authority in corresponding application PCT/US16/47031 dated Jan. 12, 2017.
EPO Office Action in corresponding U.S. Appl. No. 16/839,815 dated Sep. 26, 2019.
PCT IPRP in corresponding application PCTUS2016047031 dated Feb. 27, 2018.
AU Examination Report for related application AU 2021269355 dated Nov. 2, 2022.
AU Examination Report for corresponding application AU 2023202032 dated Feb. 28, 2024.
NZ Examination Report for related application NZ 739971 dated Oct. 19, 2020.

(56) References Cited

OTHER PUBLICATIONS

NZ Examination Report for related application NZ 739971 dated Apr. 12, 2021.
NZ Examination Report for related application NZ 739971 dated Aug. 11, 2021.
NZ Examination Report for corresponding application NZ 779020 dated Jul. 18, 2023.
EP Search Report for related application EP 23153159.1 dated May 19, 2023.
EP Partial Search Report for related application EP 16839815.4 dated May 14, 2019.
EP Partial Search Report for related application EP 16839815.4 dated Oct. 9, 2019.

* cited by examiner

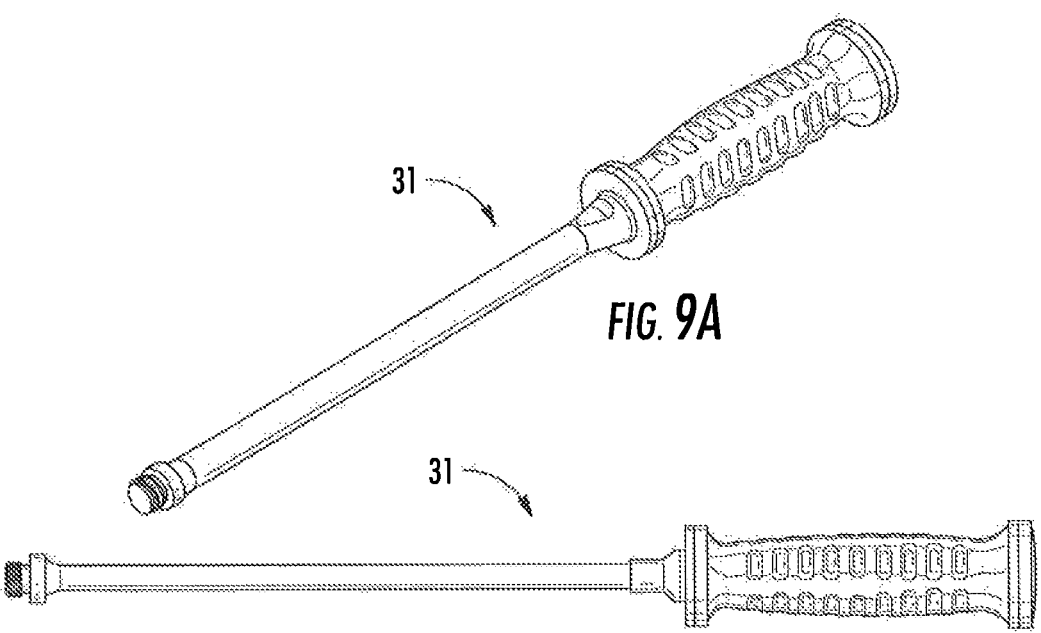
FIG. 9A
FIG. 9B
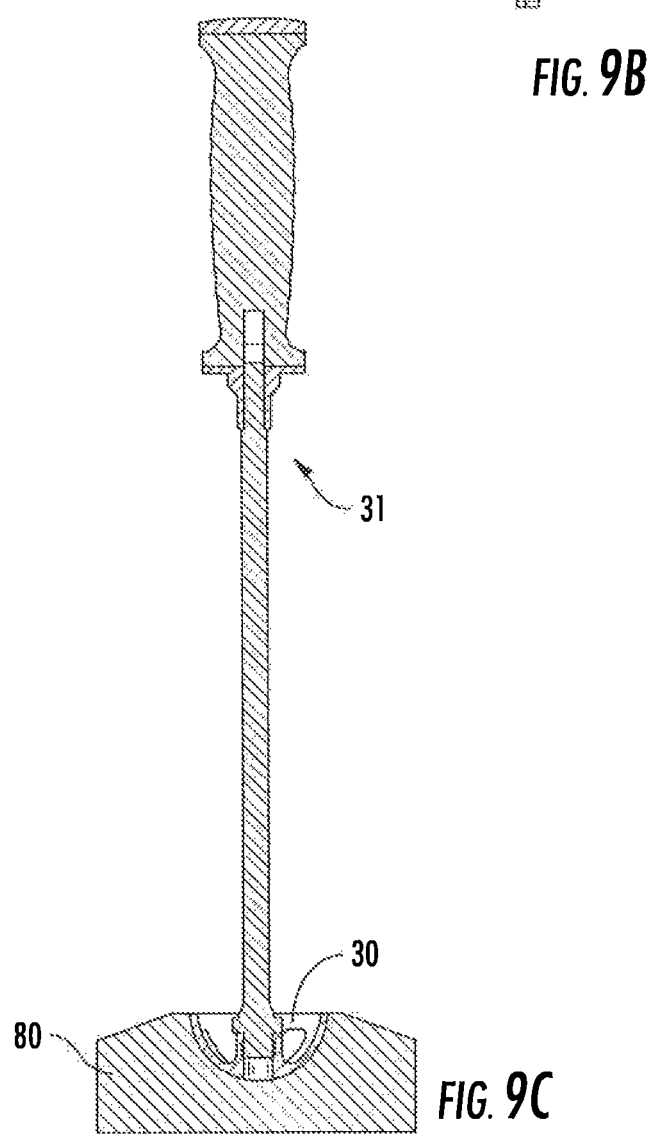
FIG. 9C

SURGICAL TRAYS, INSTRUMENTS AND METHODS FOR IMPLANTING A HIP REPLACEMENT PROSTHESIS

This is a divisional patent application of copending application U.S. Ser. No. 15/746,304, filed on 19 Jan. 2018, which in turn was an application filed under 35 USC 371 based on PCT/US2016/047031, which in turn is based on U.S. Ser. No. 62/208,127, filed 21 Aug. 2015. The present application claims the full priority benefit of these prior applications and herein incorporates by reference the full disclosures of these prior applications.

BACKGROUND OF THE INVENTION

Field of the Invention

The present invention relates to surgical instruments and methods used in connection with a reverse hip prosthesis. More particularly, the invention has to do with instrument trays, surgical tools, and trial implants used in hip replacement surgery.

The Related Art

A reverse hip prosthesis is described in U.S. Pat. Nos. 8,313,531 B2 and 8,540,779 B2. The prosthesis and a revision surgery method also are described in U.S. Pat. No. 8,992,627 B2. The disclosures of these three patents are incorporated herein in their entireties by reference.

SUMMARY OF THE INVENTION

As described in the patents referenced above, the reverse hip prosthesis generally comprises an acetabular ball affixed to a stem in an acetabular cup and a femoral cup affixed to a femoral stem wherein the femoral cup articulates on the acetabular ball. The surgical trays, tools, and methods of the invention enable a surgeon to identify the optimum components of the reverse hip prosthesis based on size and angles, for implantation in a patient using trial implants and specialized surgical tools. In the present disclosure we use the term "tools" from time to time to mean surgical tools.

BRIEF DESCRIPTION OF THE DRAWINGS

FIGS. 9A, 9B and 9C illustrate in perspective and elevation a handle used to install and remove a trial acetabular cup and a section view of the handle threaded into the trial acetabular cup which is in a representative section of an acetabulum.

DETAILED DESCRIPTION OF THE PREFERRED EMBODIMENTS

Figures 1A, 1B:
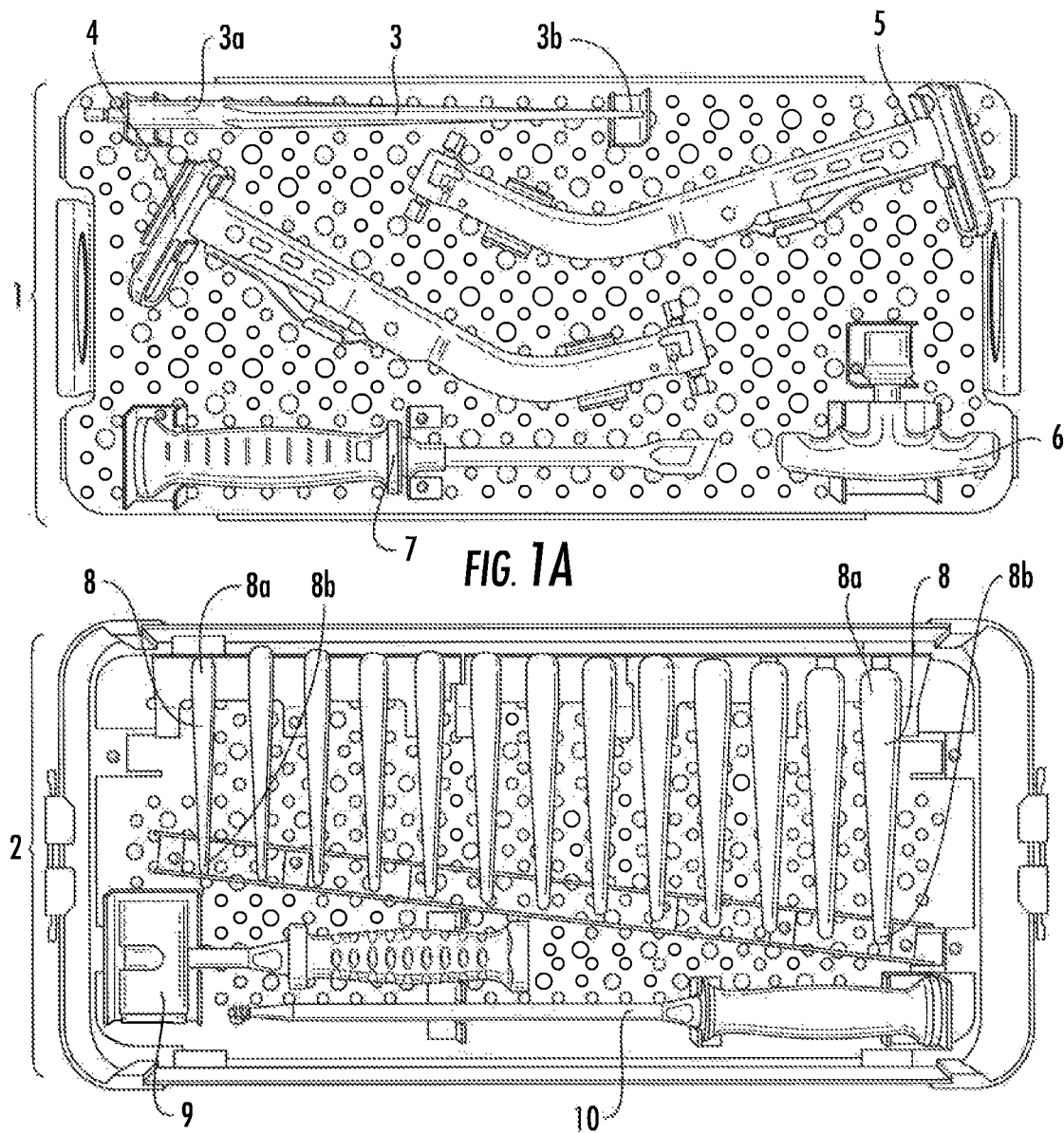
FIGS. 1A and 1B illustrate of a set of trays containing tools for preparing a femur for implant surgery.

The tools used to prepare a femur for hip implant surgery are contained in a first set of steel trays 1 and 2 of FIGS. 1A and 1B, respectively. Tray 1 contains a reamer 3, a right handed handle 4 and a left handed handle 5. Also included in tray 1 are a T-handle 6 and a box osteotome 7. After the femur has been prepared for surgery by cutting off the femoral head, the box osteotome 7 is used as a center punch to make an initial opening in the femur as a guide for correct positioning of the reamer 3. Then the T-handle 6, which is adapted for connection to the proximal end 3a of reamer 3, is affixed to the reamer and the surgeon places the distal end 3b of reamer 3 into the initial opening and turns the handle while applying pressure to create a pocket in the femur. The right and left handed handles, 4 and 5 respectively, are adapted for connection to the proximal end 3a of the reamer for rotating the reamer to make a deep pocket in the femur in preparation for use of the broaches 8 as explained below in connection with tray 2. The right handed handle 4 is used by a right handed surgeon and the left handed handle 5 is used by a left handed surgeon.

Tray 2 contains a set of two or more than two different sized broaches 8. The broaches have sizes ranging from 9 mm (on the left hand side of FIG. 1B) to 21 mm (on the right hand side of FIG. 1B). In the drawing, each broach 8 going from left to right is 1 mm larger than the one to the left. As can be seen from the drawing, the broaches are tapered and the size of each broach refers to the maximum diameter at the top, the proximal end 8*a*, of the broach. The broach 8, also known as a rasp, is inserted into the deep pocket and pounded at the proximal end 8*a*, using hammer 9, into the femur. Handle 10 is threaded into the threaded recess 75*a* at or near the proximal end of the femoral implant 75 (see FIG. 13) and is used to implant the femoral implant into the femur.

Figure 2A:
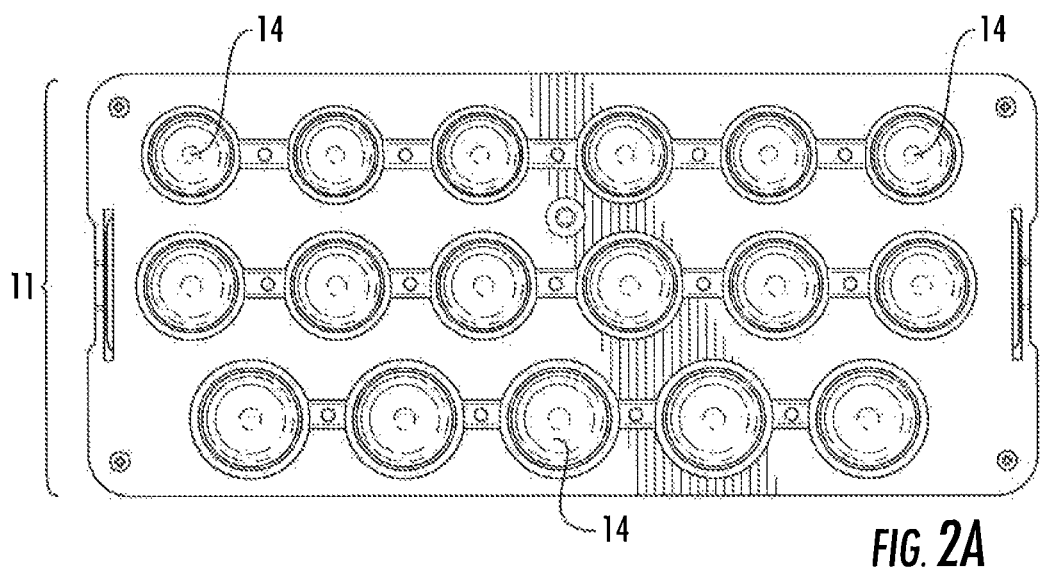
FIGS. 2A, 2B and 2C illustrate of a set of trays containing tools for preparing an acetabulum for implant surgery.
Figure 2B:
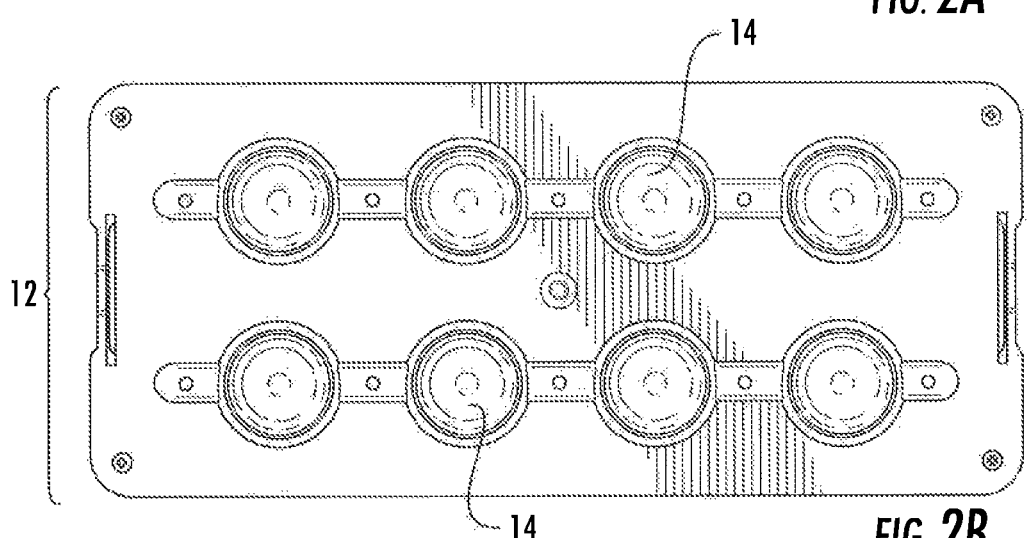
Figure 2C:
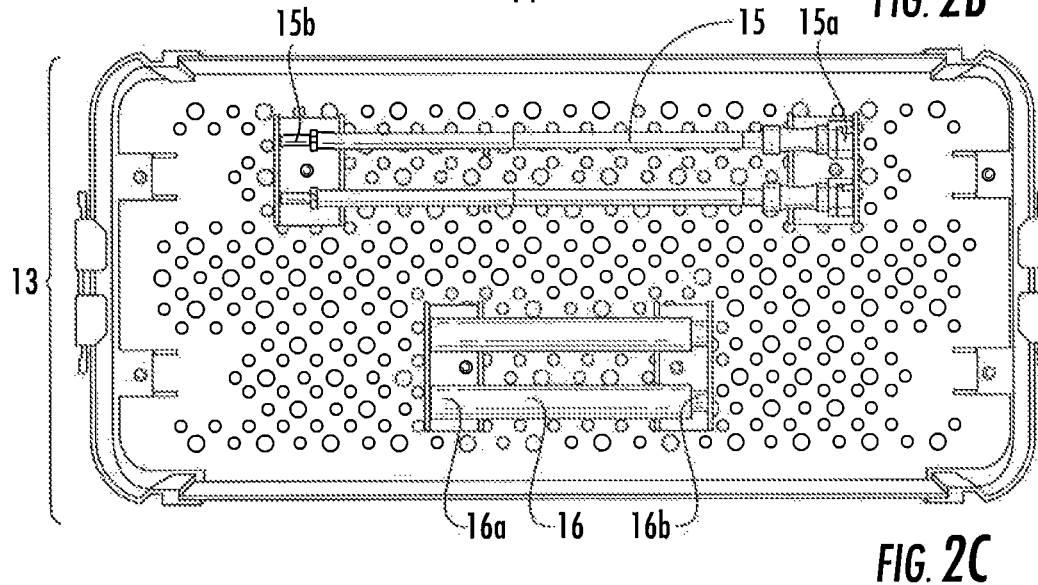
Figure 23:
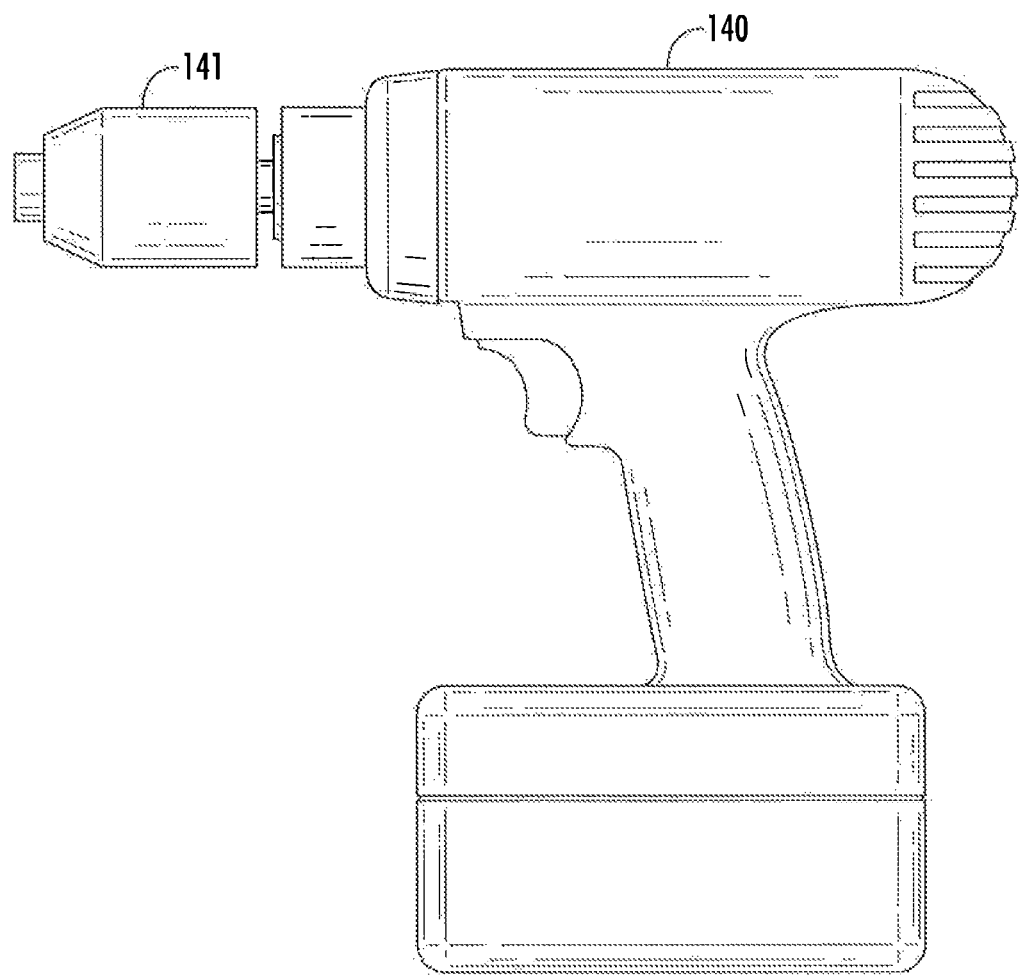
FIG. 23 is an elevation view of a conventional electric drill used in surgery.

The tools used to prepare an acetabulum for hip transplant surgery are contained in a second set of steel trays 11, 12 and 13 of FIGS. 2A, 2B and 2C, respectively. Trays 11 and 12 cumulatively contain two or more than two (twenty-five being illustrated in FIGS. 2A and 2B) different sized acetabular bone cutters 14 which are used to cut the acetabular bone to the appropriate size to receive a correspondingly sized acetabular cup. A drive shaft and a drive shaft handle are used to connect a drill 140 (see FIG. 23) to acetabular bone cutters 14. Tray 13 illustrates two different sized drive shafts 15 and two drive shaft handles 16. The drive shaft has a distal end 15*b* adapted for connection to a bone cutter and a proximal end 15*a* adapted for connection to the distal end 16*b* of a drive shaft handle 16. The proximal end 16*a* of the drive shaft handle 16 is adapted for connection to chuck 141 of the drill 140.

Figure 3A:
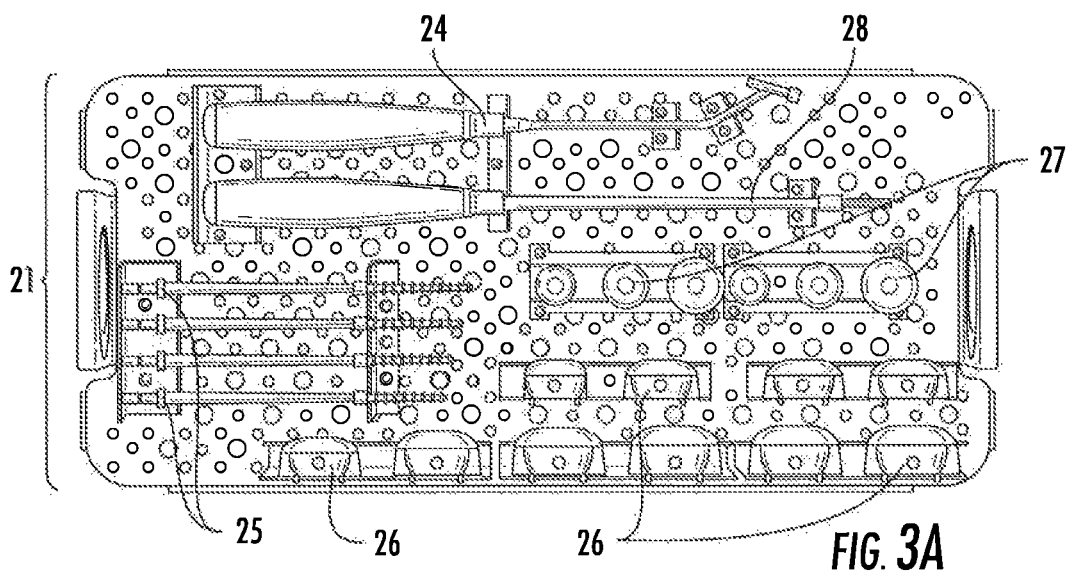
FIGS. 3A, 3B and 3C illustrate of a set of trays containing trial implants and tools for sizing and implanting the acetabular cup and the acetabular ball.
Figure 3B:
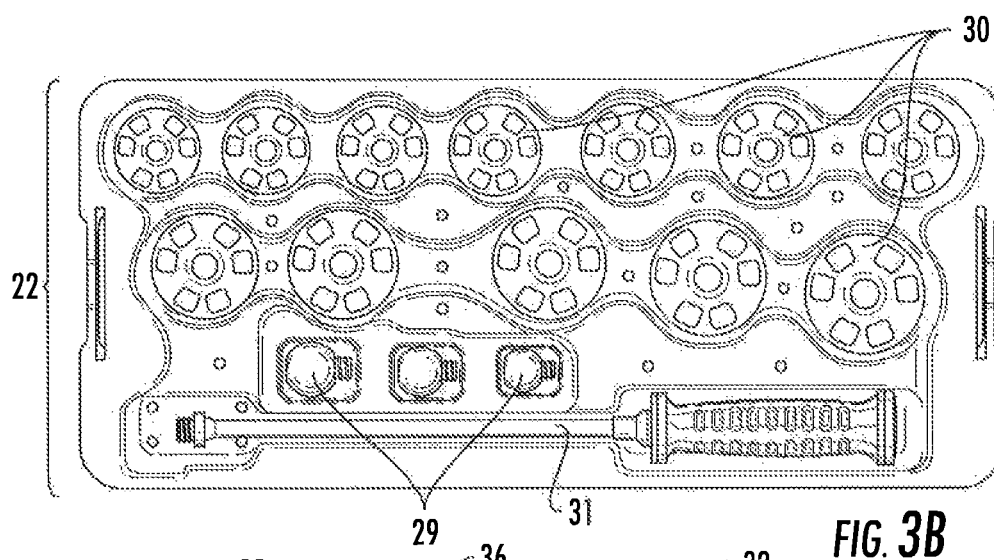
Figure 3C:
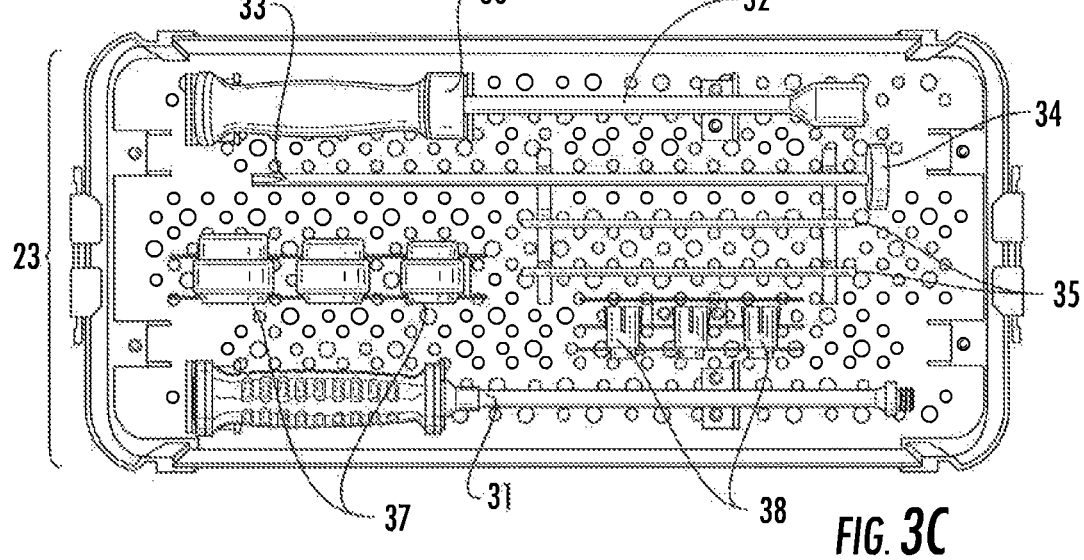

Trial implants and tools for implanting an acetabular cup and an acetabular ball are contained in a third set of steel trays 21, 22 and 23 of FIGS. 3A, 3B and 3C respectively.

Tray 21 contains a drill guide handle 24, two or more than two drill bits 25, two or more than two drill guides 26, two or more than two second trial acetabular balls 27 and a trial acetabular ball insertion-removal tool 28. Each drill bit 25 has a correspondingly sized drill guide.

Tray 22 contains two or more than two first trial acetabular balls 29, two or more than two trial acetabular cups 30 and a universal handle 31.

Tray 23 contains elements of an acetabular cup impactor assembly. This includes another universal handle 31, an acetabular cup handle 32, an inner shaft 33 having a knob 34 at the proximal end thereof, two anteversion guide rods 35, at least one and preferably three collets 38 and at least one and preferably three acetabular ball impactors 37. The inclination and anteversion guide 36 has a thumb screw (not shown) for maintaining the guide 36 in the appropriate position on the acetabular cup handle 32. This is described in detail in our co-pending international application No. PCT/US 16/42441 filed on Jul. 15, 2016.

Figure 4A:
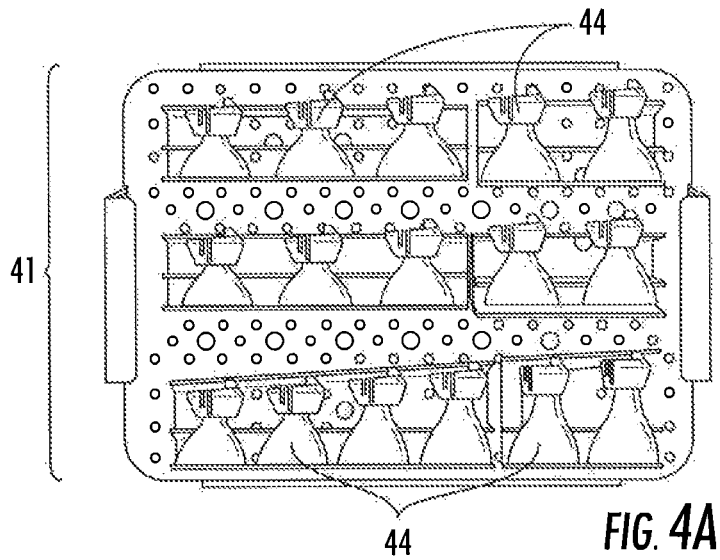
FIGS. 4A, 4B, and 4C illustrate of a set of trays containing trial implants and tools for sizing and implanting the femoral cup.
Figure 4B:
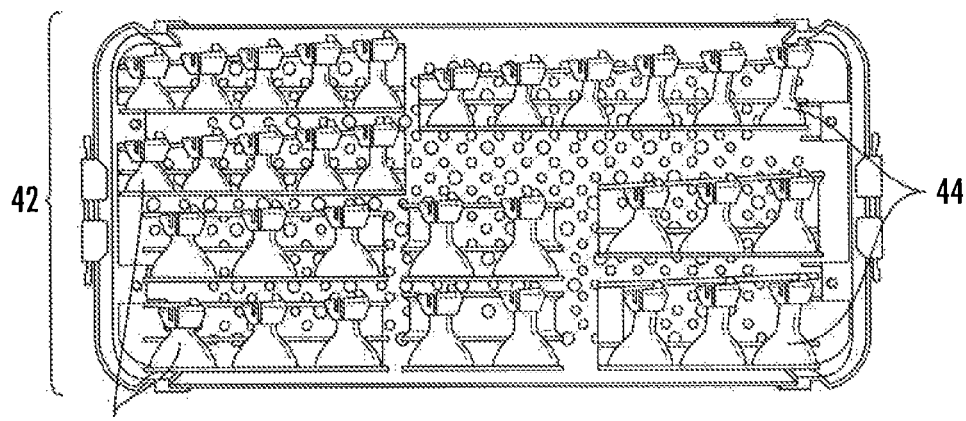
Figure 4C:
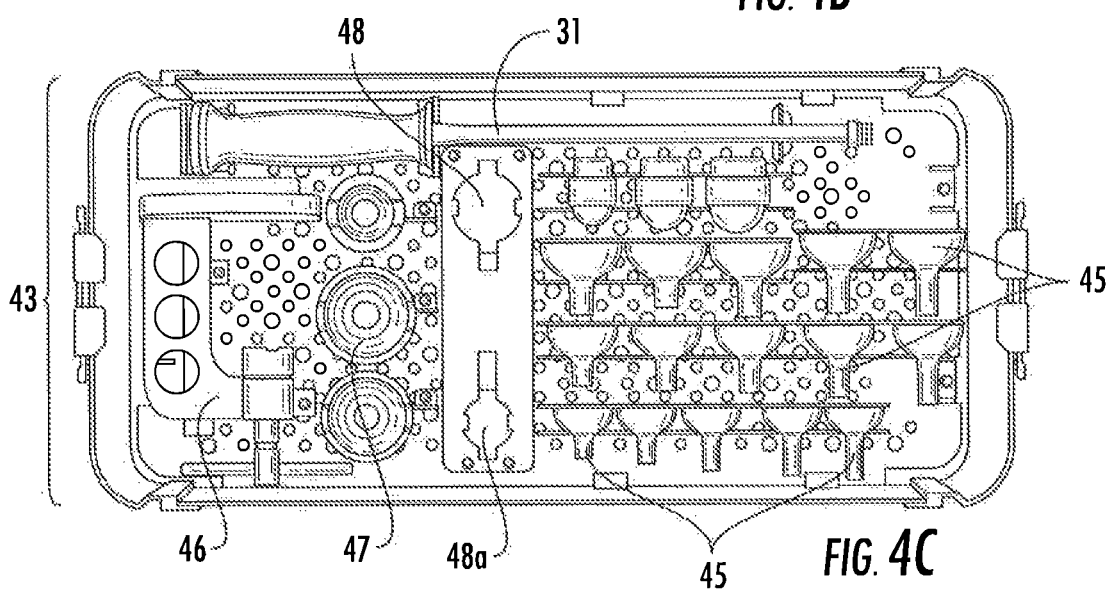

Trial implants and tools for implanting a femoral cup are contained in a fourth set of steel trays 41, 42, and 43, of FIGS. 4A, 4B and 4C respectively.

Trays 41 and 42 only contain two or more than two first trial femoral cups 44. These first trial femoral cups 44 may vary in size, neck length and offset angle. They are preferably adapted to be temporarily affixed to the proximal end of a broach 8 from tray 2 before the broach is removed from the femur. Alternatively, they can be temporarily affixed to the proximal end of a femoral implant 49 as shown in FIGS. 11E and 11F.

Figure 16A:
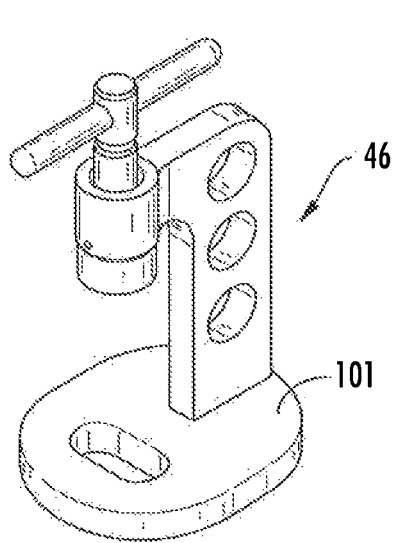
FIGS. 16A, 16B, 16C, 16D, 16E, 16F, 16G and 16H illustrate various views of a press assembly and components thereof, the press assembly being used to press a liner in a femoral cup.
Figure 16B:
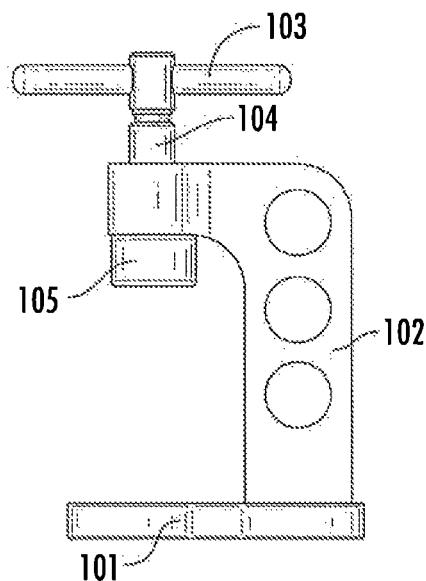
Figure 16C:
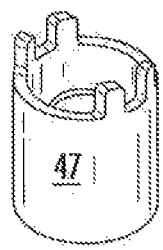
Figure 16D:
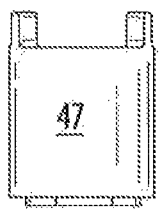
Figure 16E:
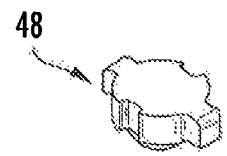
Figure 16F:
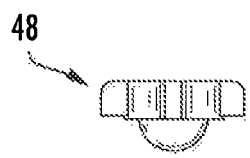
Figure 16G:
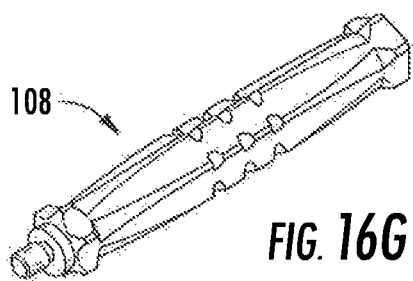
Figure 16H:
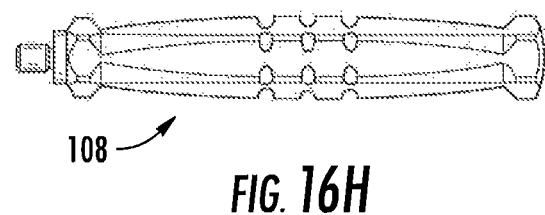
Figure 18:
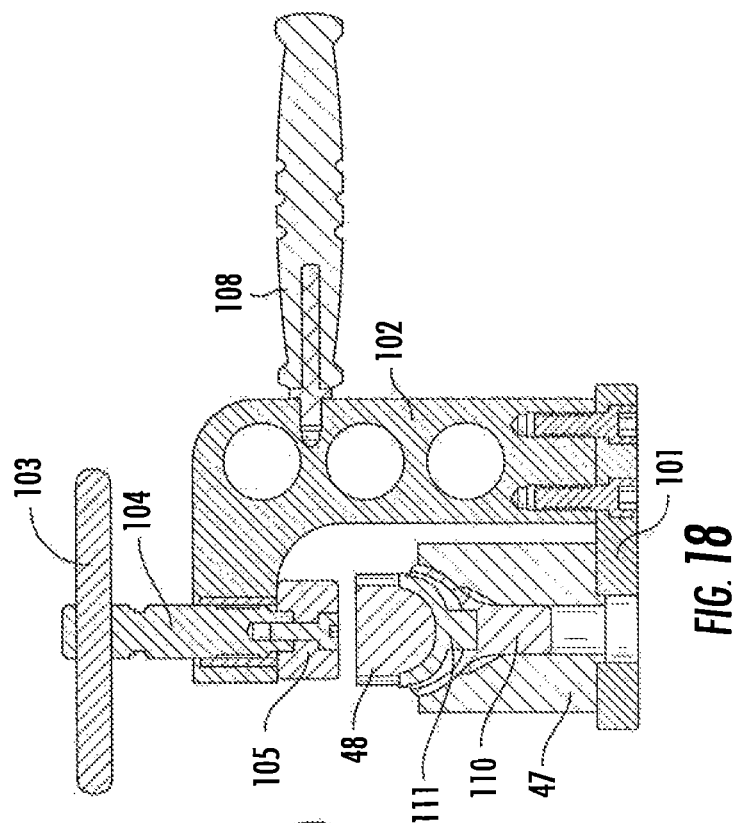
FIG. 18 is a section view of FIG. 17.
Figure 17:
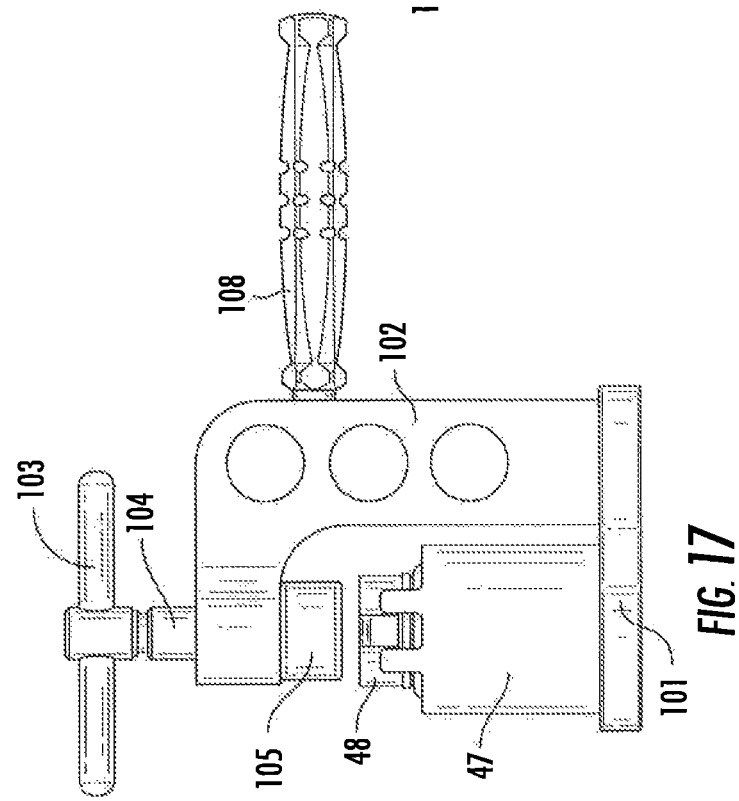
FIG. 17 is an elevation view of the press assembly of FIGS. 16A-H with a femoral cup therein.

Tray 43 contains two or more than two second trial femoral cups 45 which are adapted to be temporarily affixed to the femoral implant 49. (See FIGS. 11E and 11F.) The tray also contains a press 46, femoral cup locator 47 and plungers 48 and 48*a* for pressing a polymer liner into a femoral cup. (See also FIGS. 16C, D, E and F.)

Figure 5A:
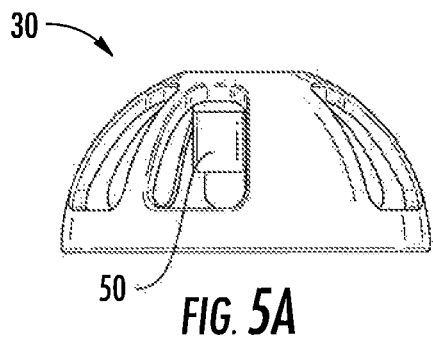
FIGS. 5A, 5B, 5C, 5D and 5E include elevation, section and perspective views of a trial acetabular cup.
Figure 5B:
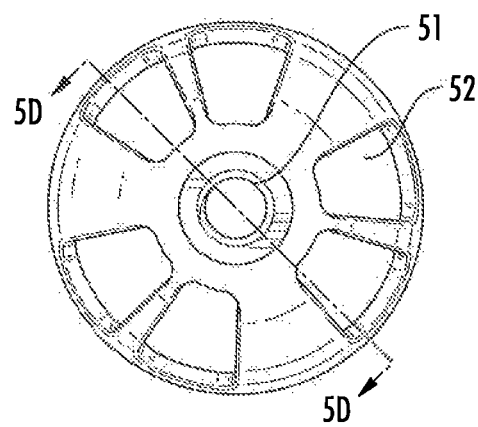
Figure 5C:
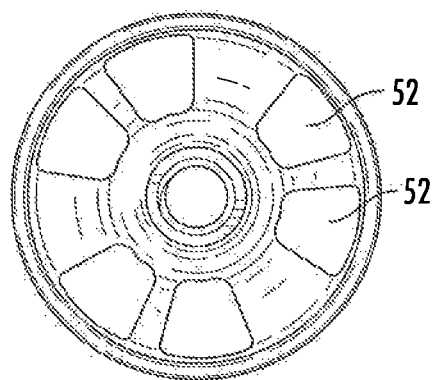
Figure 5D:
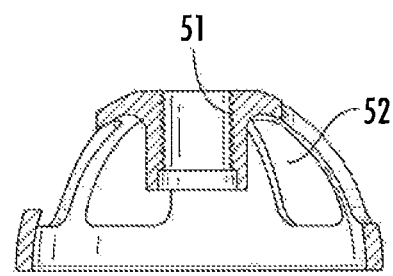
Figure 5E:
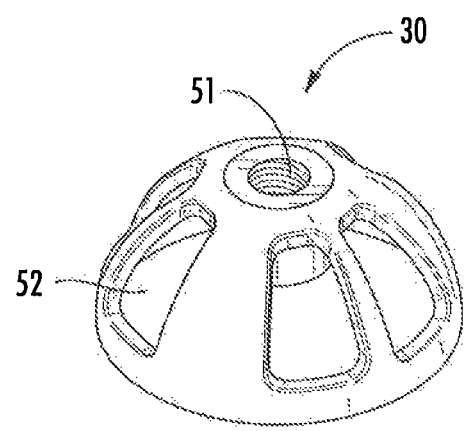

Turning more specifically to the various components contained in the trays discussed above, FIGS. 5A-5E illustrate various views of the trial acetabular cups 30. FIG. 5E is a perspective view of a trial acetabular cup. FIG. 5A is a side elevation view and FIG. 5D is a section view of FIG. 5A. FIG. 5B is a top elevation view and FIG. 5C is a bottom elevation view.

Figure 6A:
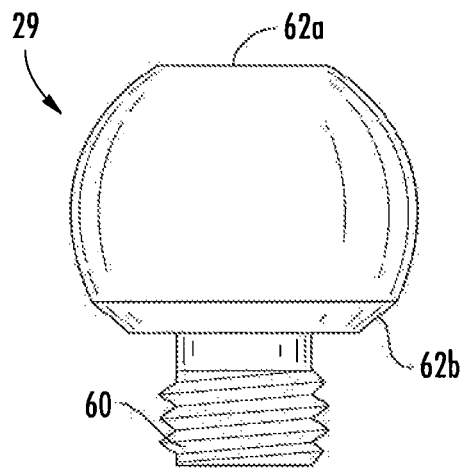
FIGS. 6A, 6B, 6C and 6D include elevation, section and perspective views of a first trial acetabular ball for use with the trial acetabular cup.
Figure 6B:
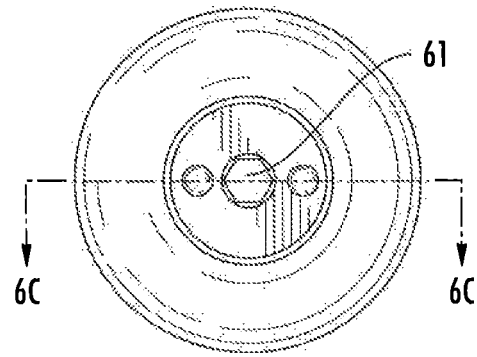
Figure 6C:
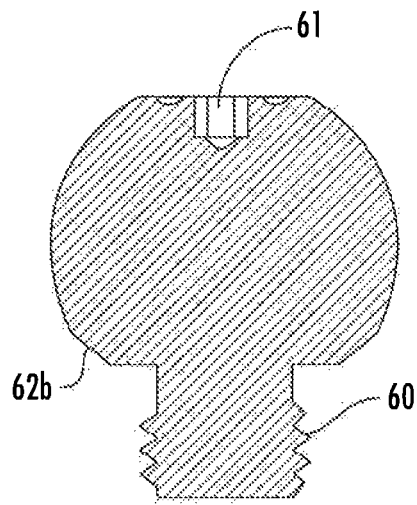
Figure 6D:
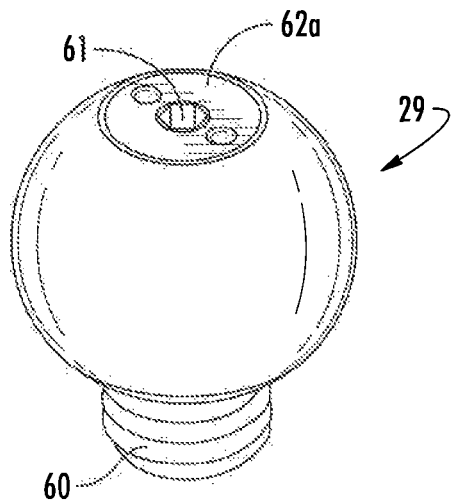

Trial acetabular cup 30 has an outer surface adapted to fit in a prepared surface of an acetabular bone and an inner concave surface. The outer surface preferably is a convex surface. A stem 50 with an internally threaded opening 51 extends from the bottom of the concave surface and the cup is characterized by multiple optional through openings 52. The threaded opening 51 receives the threads of universal handle 31 which is used to install and remove the cup 30 from the acetabulum. (See FIG. 9C.) The threads of opening 51 also receive the first trial acetabular balls 29 which are illustrated in FIGS. 6A-6D. The trial acetabular balls of the invention are hemispherical and may include flattened portions and bevels as described below. FIG. 6D is a perspective view of a trial acetabular ball 29, FIG. 6A is a side elevation view, FIG. 6B is a top elevation view and FIG. 6C is a section view. The threaded portion 60 is threaded into opening 51. A hexagonal opening 61 is illustrated in flattened portion 62*a* and accommodates tool 28 (see FIG. 3A) which is used to thread ball 29 into and out of cup 30. Optional beveled portion 62*b* is proximate to the threaded portion 60 and creates a beveled edge surrounding the base of the ball 29.

FIGS. 7 and 8 have to do with a second trial acetabular ball 27.

FIGS. 7A-7F illustrates various views of said ball 27. The ball 27 can be temporarily affixed to an implanted acetabular cup 70 (see FIGS. 8D and 8E) in order to determine the optimum ball size for the prosthesis. FIGS. 8A-8C illustrate the second trial acetabular ball 27 in a different size.

Figure 7A:
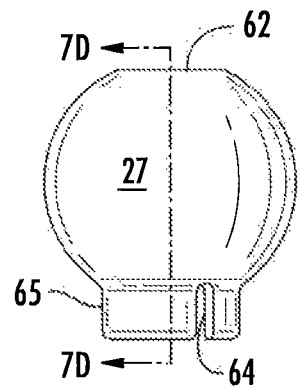
FIGS. 7A, 7B, 7C, 7D, 7E and 7F include elevation, section, detail and perspective views of a second trial acetabular ball for use with an implanted acetabular cup.
Figure 7B:
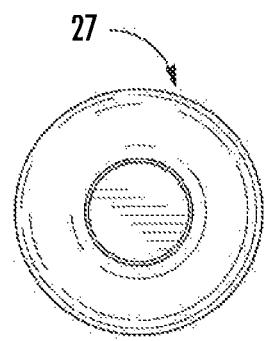
Figure 7C:
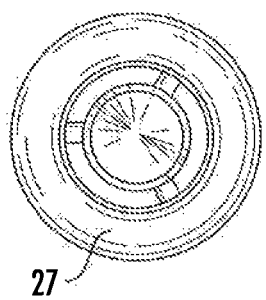
Figure 7D:
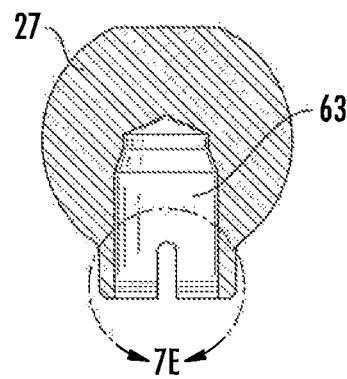
Figure 7E:
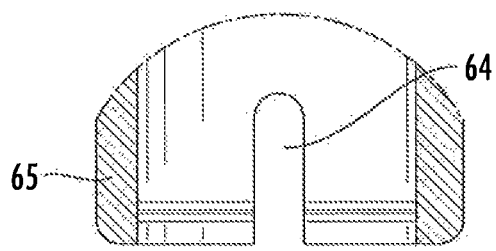
Figure 7F:
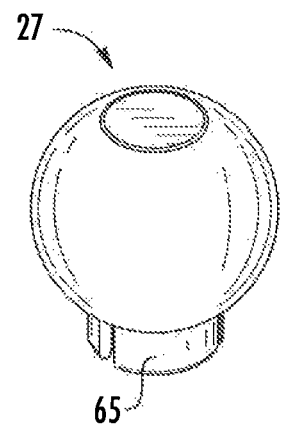
Figure 8A:
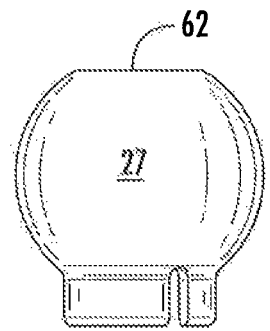
FIGS. 8A, 8B, 8C, 8D and 8E include illustrate various views of the second trial acetabular ball, the type illustrated in FIGS. 7A-F, and elevation and section views of said ball placed over the stem of an acetabular cup.
Figure 8B:
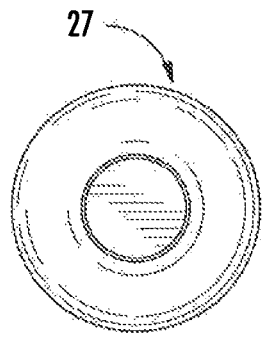
Figure 8C:
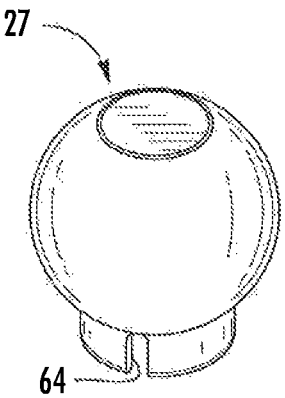
Figure 8D:
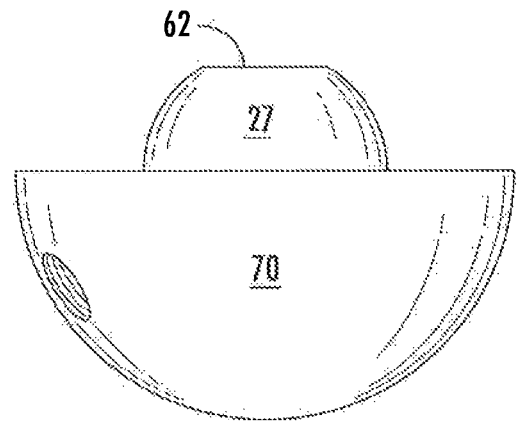
Figure 8E:
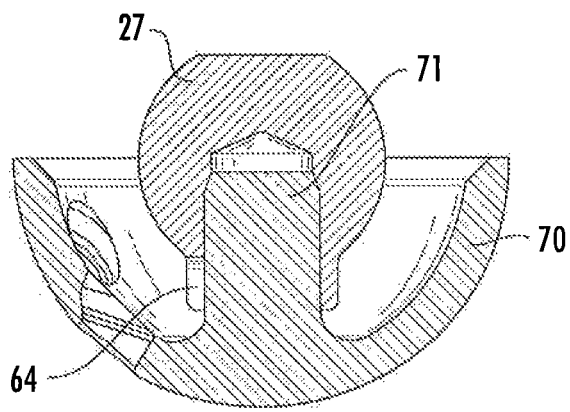

FIGS. 7F and 8C are perspective views of ball 27, FIGS. 7A and 8A are side elevation views of ball 27 and FIGS. 7B and 8B are top elevation views. FIG. 7C is a bottom elevation view of ball 27 and FIG. 7D is a section view taken along section line 7D of FIG. 7A. A detail view of encircled portion 7E of FIG. 7D is shown in FIG. 7E.

Second trial acetabular ball 27 is comprised of a flattened top portion 62 which is used to imprint identifying size information. The ball 27 has an opening 63 which is sized to fit over the stem 71 of acetabular cup 70. A slot 64 is provided on the side of projection 65 to make it easier to place the ball on stem 71 and to remove it from the stem.

A universal handle 31 is illustrated in a side elevation view in FIG. 9B and a perspective view in FIG. 9A. FIG. 9C is a section view of universal handle 31 threaded into trial acetabular cup 30 which is in a representative portion of acetabular bone 80. Handle 31 is used to place trial cup 30 into acetabular bone 80.

Multiple views of a first trial femoral cup 44 are illustrated in FIG. 10. FIG. 11 illustrates more views of cup 44 as well as views of cup 44 in a femoral implant 49.

Figure 10A:
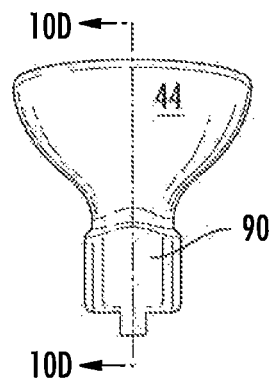
FIGS. 10A, 10B, 10C, 10D, 10E and 10F include elevation, section, detail and perspective views of a first trial femoral cup.
Figure 10B:
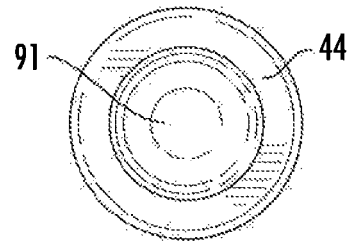
Figure 10C:
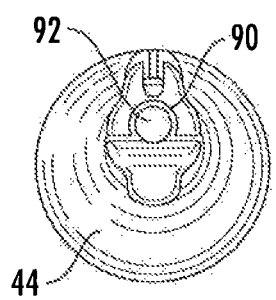
Figure 10D:
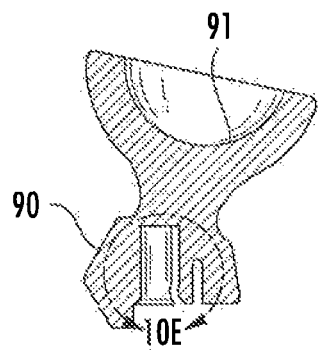
Figure 10E:
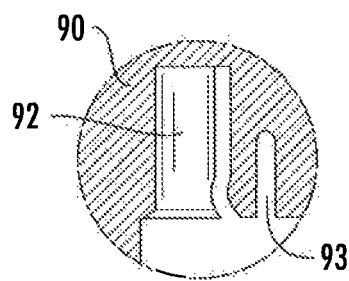
Figure 10F:
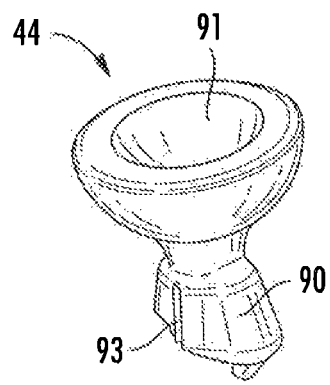
Figure 11A:
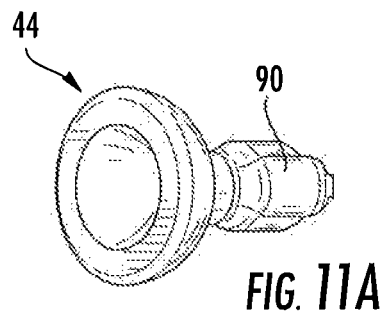
FIGS. 11A, 11B, 11C, 11D, 11E and 11F include additional views of the first trial femoral cup, the type illustrated in FIGS. 10A-F, and perspective and elevation views of said cup in a first femoral implant.
Figure 11B:
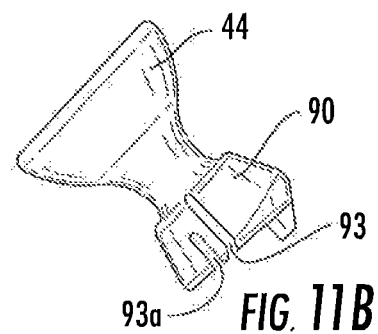
Figure 11C:
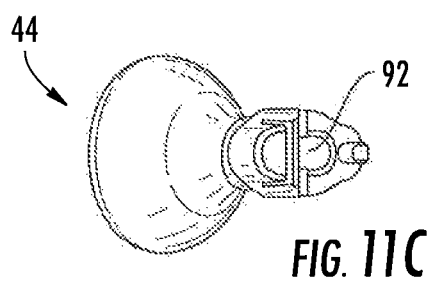
Figure 11D:
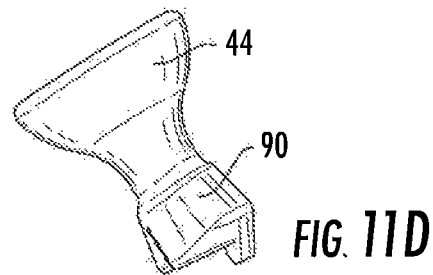
Figure 11E:
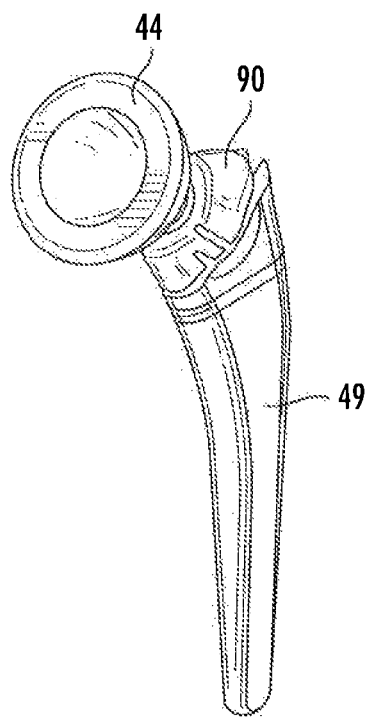
Figure 11F:
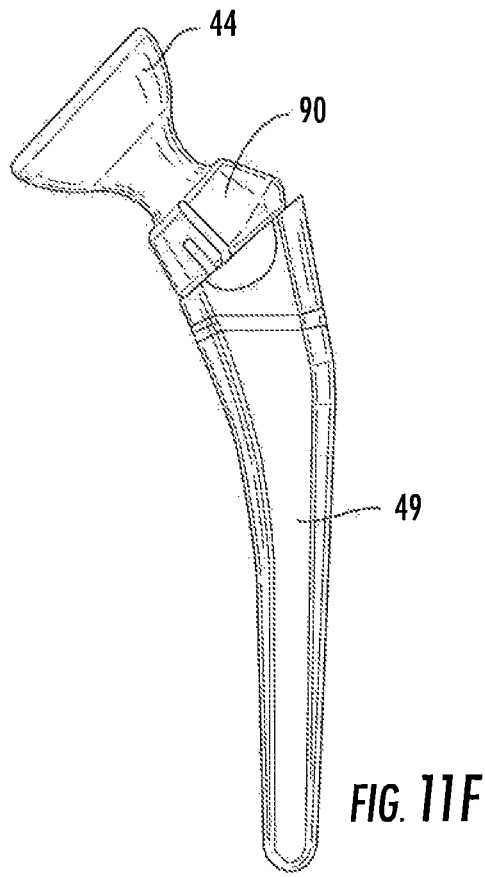

Three different perspective views of first trial femoral cup 44 are illustrated in FIGS. 10F, 11A and 11C. Side elevation views of the cup 44 taken from different angles are illustrated in FIGS. 10A, 11B and 11D. FIG. 10B is a top elevation view, FIG. 10C is a bottom elevation view and FIG. 10D is a section view taken along section line 10D of FIG. 10A. FIG. 10E is a detail view taken from encircled portion 10E of FIG. 10D. FIG. 11F is a side elevation view of cup 44 affixed to implant 49 and FIG. 11E is a perspective view of cup 44 affixed to implant 49.

First trial femoral cup 44 has a base portion 90 in the form of a stem extending away from (i.e. opposite from) first concave portion 91. Included within base portion 90 is an opening 92 which receives the proximal end of a broach 8 or a stem of an implant 49. Slots 93 and 93a are provided to make it easier to place the cup on a broach or a stem and then remove it.

Figure 12A:
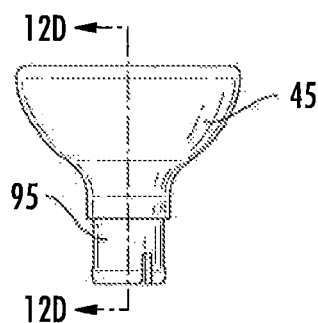
FIGS. 12A, 12B, 12C, 12D, 12E and 12F illustrate elevation, section, detail and perspective views of a second trial femoral cup.
Figure 12B:
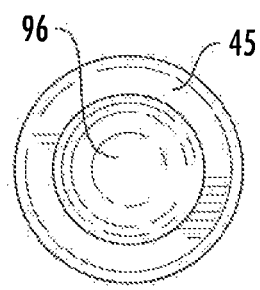
Figure 12C:
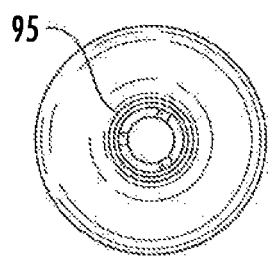
Figure 12D:
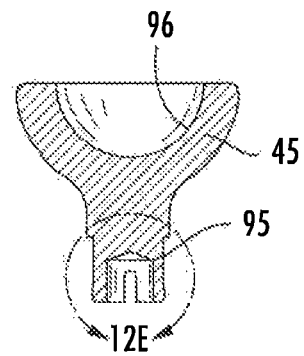
Figure 12E:
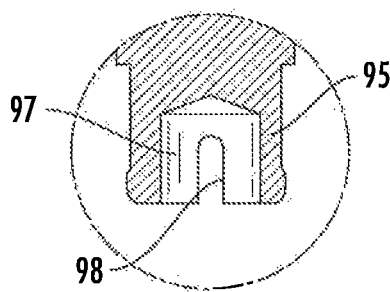
Figure 12F:
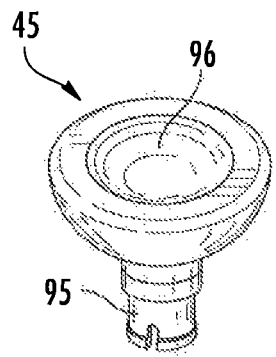
Figure 13A:
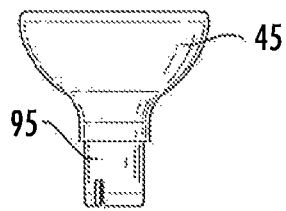
FIGS. 13A, 13B, 13C, 13D, 13E, 13F and 13G illustrate additional views of the second trial femoral cup, the type illustrated in FIGS. 12A-F, and perspective, elevation and section views of said cup in a second femoral implant.
Figure 13B:
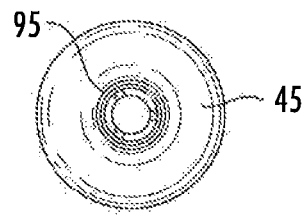
Figure 13C:
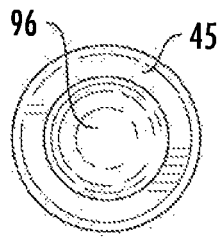
Figure 13D:
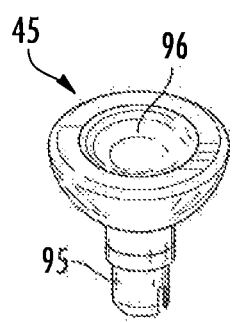
Figure 13E:
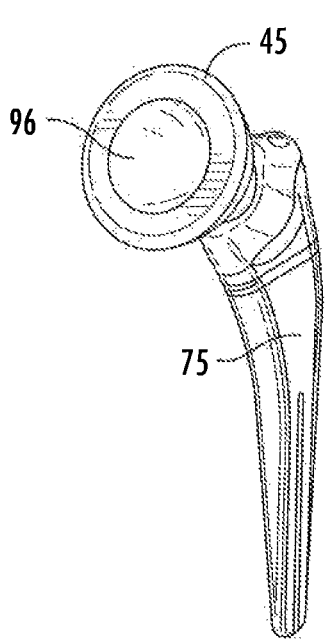
Figure 13F:
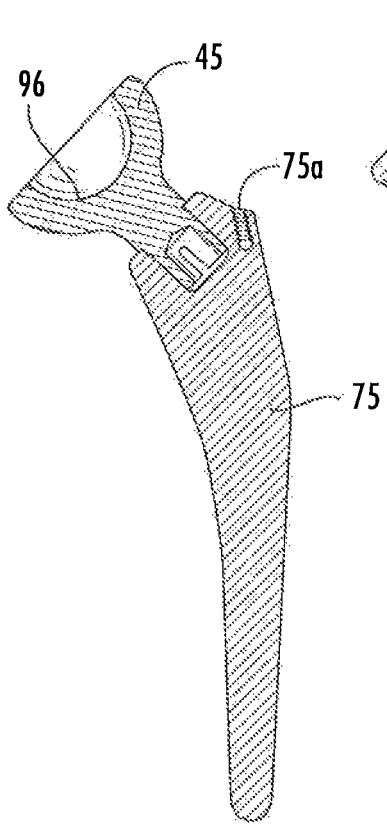
Figure 13G:
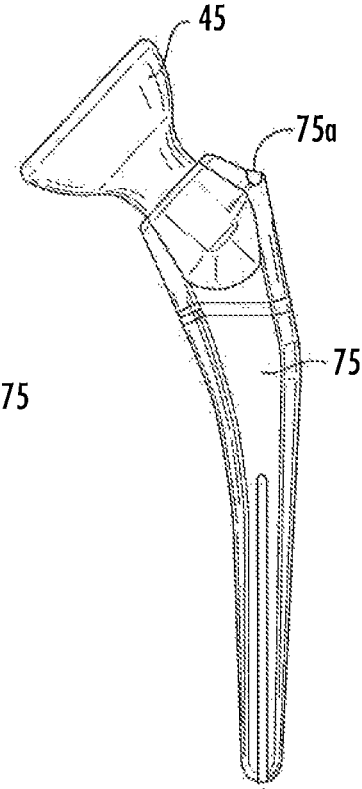

Second trial femoral cup 45 is illustrated in multiple views in FIGS. 12A-F. FIGS. 13A-G illustrate more views of cup 45 as well as views of cup 45 in femoral implant 75. Perspective views of cup 45 are illustrated in FIGS. 12F and 13D, side elevation views are illustrated in FIGS. 12A and 13A, top elevation views are illustrated in FIGS. 12B and 13C and bottom elevation views are illustrated in FIGS. 12C and 13B. FIG. 12D is a section view taken along section line 12D of FIG. 12A and FIG. 12E is a detail view taken from encircled portion 12E of FIG. 12D. FIG. 13E is a perspective view of cup 45 in implant 75, FIG. 13G is a side elevation view of cup 45 in implant 75 and FIG. 13F is a section view of FIG. 13G.

Second trial femoral cup 45 has a stem 95 which extends away from second concave portion 96 and which is adapted to be received within a femoral implant 75. An opening 97 in stem 95 works in coordination with slot 98 to facilitate attaching cup 45 to femoral implant 75 and removing it therefrom.

Figure 14:
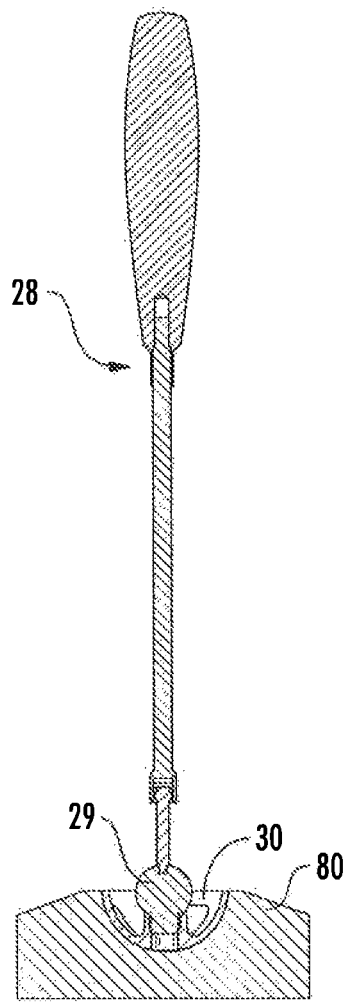
FIG. 14 is a section view illustrating a first trial acetabular ball in a trial acetabular cup and a tool used to attach and remove said ball from said cup.

FIG. 14 illustrates in section the trial acetabular ball insertion-removal tool 28 inserted into the hexagonal opening of trial acetabular ball 29. This is the position of the tool relative to the ball for threading the ball into or out of trial acetabular cup 30, the cup 30 shown in the representative portion of acetabular bone 80.

Figure 15:
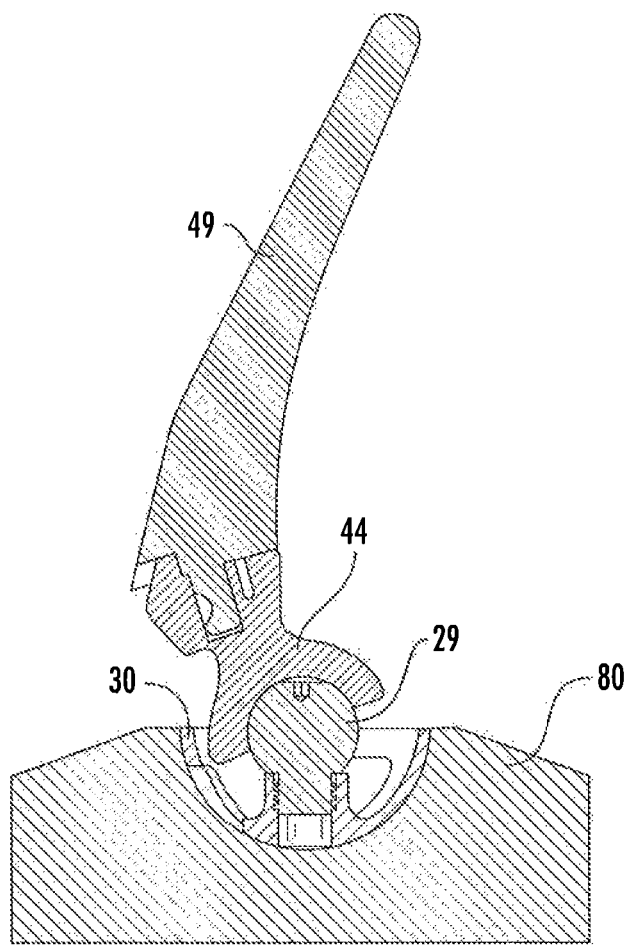
FIG. 15 is a section view illustrating a first trial femoral cup in an articulating position on a first trial acetabular ball.

A trial femoral cup 44 is shown in position on trial acetabular ball 29 in FIG. 15. The femoral cup 44 is attached to implant 49 and trial acetabular cup 30 is shown in acetabular bone 80.

The elements of a press 46 which is used to press a polymer liner into the femoral cup are illustrated in FIG. 16. A perspective view of press 46 is shown in FIG. 16A. Referring to FIGS. 16A-16F and FIGS. 17 and 18, the press is comprised of a base 101 having a bracket 102 affixed thereon. A press bar 103 is provided on shaft 104 and a cylinder 105 is provided at the distal end of shaft 104. The cylinder 105 contacts and presses upon an appropriately sized plunger 48. The femoral cup locator 47 having a femoral cup 110 therein is positioned on base 101. The concave portion of a polymer liner 111 is positioned on plunger 106 and the convex portion of liner 111 is positioned over the concave portion of femoral cup 110 as illustrated in section in FIG. 18. Then the plunger 48 is pushed downwardly using press bar 103 to cause cylinder 105 to contact and press downwardly upon the plunger while also holding stabilizing handle 108 until liner 111 snaps into place in the concave portion of femoral cup 110.

Figure 20:
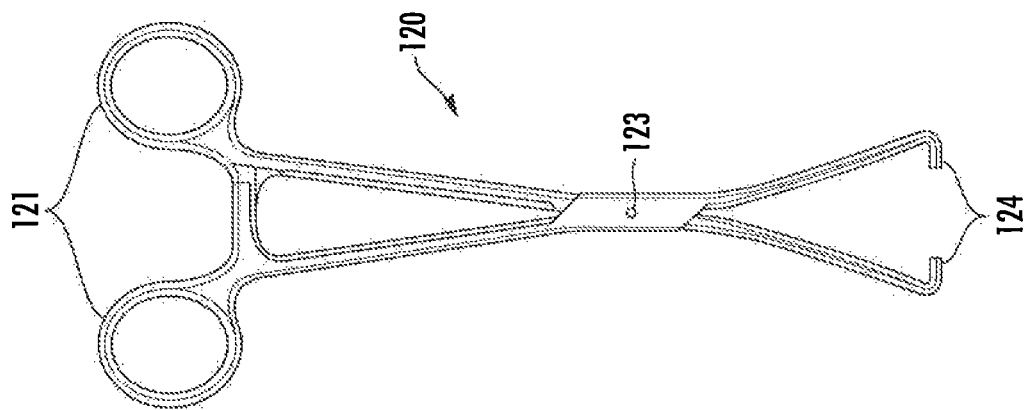
FIG. 20 is an elevation view of the tool of FIG. 19.
Figure 19:
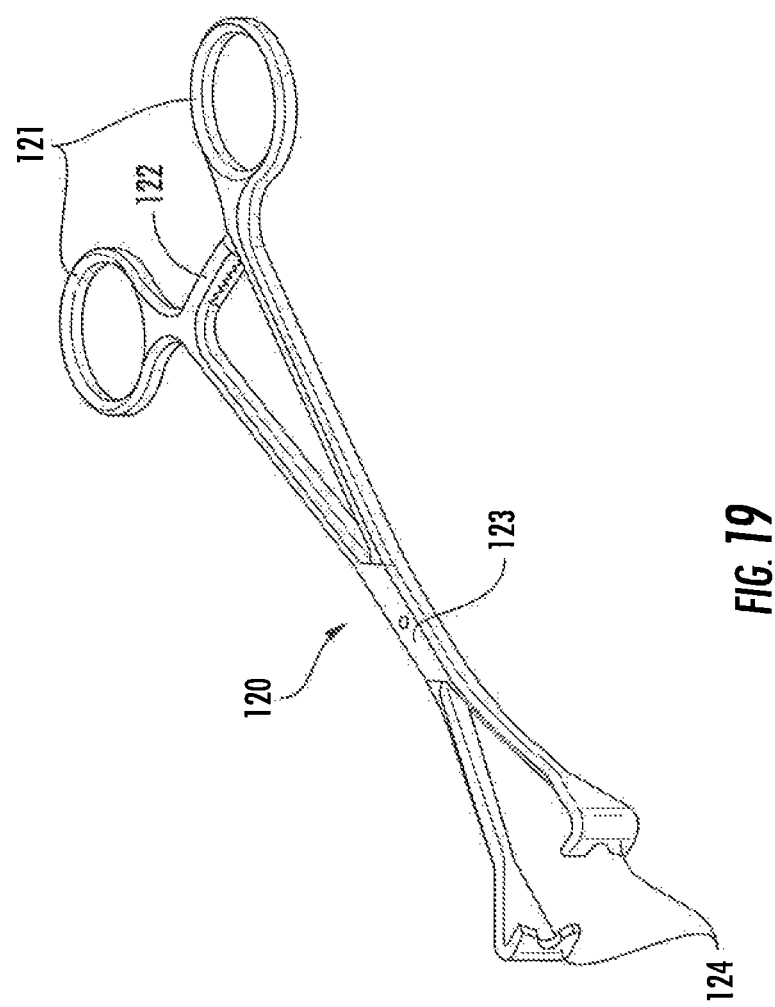
FIG. 19 is a perspective view of an insertion-removal tool.
Figure 21:
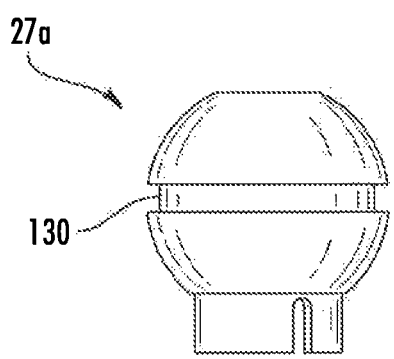
FIG. 21 is an elevation view of another embodiment of a trial acetabular ball adapted for use with the insertion-removal tool.

Insertion-removal tool 120 is illustrated in FIGS. 19 and 20. The tool is similar to a hemostat in size and construction. The tool comprises handles 121 at its proximal end and a ratcheting portion 122. A hinge 123 is positioned to provide leverage and grippers 124 are disposed at the distal end. The portion of the tool located between the hinge 123 and grippers 124 may optionally be angled (for example at about 20°) (not shown).

Figure 22:
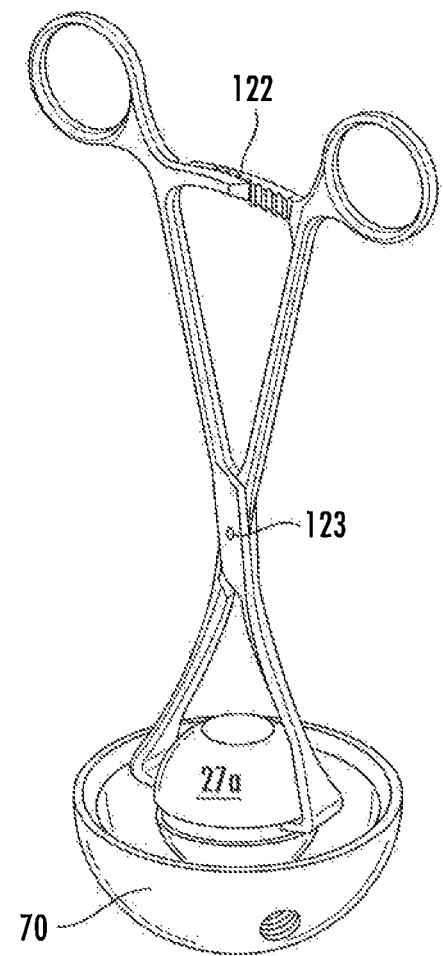
FIG. 22 is a perspective view illustrating the position of the tool of FIGS. 19 and 20 when the tool is in contact with the trial acetabular ball of FIG. 21 to facilitate removal of the ball from an acetabular cup.

In this application, the preferred use for the tool 120 is to remove a trial acetabular ball 27a from an acetabular cup 70. FIG. 22 illustrates the tool 120 positioned on ball 27a for this purpose. The ball 27a has all of the same features as ball 27 described above with the added feature of indent 130 in the form of a circumferential groove which is provided to allow gripping the ball and pulling it off of the stem 71 (see FIG. 8E) of acetabular cup 70.

The invention claimed is:

1. A surgical tray apparatus and components thereof configured for use in hip replacement surgery comprising:
   trial implants for sizing, locating and implanting a reverse hip acetabular cup including at least two differently sized trial acetabular cups each having a hemispherical outer surface and an inner concave surface, optionally one or more through openings extending through the trial acetabular cups, the inner concave surface having an internally threaded stem, the stem having a height and extending from the inner concave surface and extending to an end having an opening, and at least two differently sized first trial acetabular balls each having a threaded portion removably engageable via mating threads within the internally threaded stem of a trial acetabular cup such that when fully engaged a part of the trial acetabular ball abuts the end of the stem, and an opening centered in a flattened portion of the trial acetabular ball opposite to the threaded portion, the opening being sized and shaped to receive a tool for tightening and loosening the trial acetabular ball when the threaded portion is engaged with the mating threads of the stem of a trial acetabular cup,
   two or more than two trial femoral cups configured to be temporarily affixed to the proximal end of a broach or a femoral implant engageable with at least one of the first trial acetabular balls, each of the trial femoral cups having a base portion and a concave portion configured to articulate on a trial acetabular ball engaged with the stem of a trial acetabular cup;
   and optionally,
   at least one further article selected from: at least one tool, a press, a femoral cup locator and a plunger for pressing a polymer liner into a femoral cup.

2. The surgical tray apparatus of claim 1 comprises at least one tool for the preparation of a femur for implant surgery selected from:
   a reamer having a distal end for insertion into a femur and a proximal end;
   a right handed handle and a left handed handle configured for connection to the proximal end of the reamer;
   a T-handle configured for connection to the proximal end of the reamer;
   a box osteotome;
   two or more than two broaches each being sized to make a correspondingly sized opening in the femur;
   a hammer for pounding a broach into the femur; and
   a handle having a threaded portion configured to be threaded into a proximal end of a femoral implant.

3. The surgical tray apparatus of claim 1 comprising at least one tool for preparing an acetabulum for implant surgery selected from:
   two or more than two different sized acetabular bone cutters;
   a drive shaft having a distal end configured for connection to a bone cutter;
   a drive shaft handle configured for connection to a proximal end of the drive shaft.

4. The surgical tray apparatus of claim 3 wherein a distal end of the drive shaft handle is configured for connection to the drive shaft and a proximal end of the drive shaft handle is configured for connection to a drill.

5. The surgical tray apparatus of claim 1 comprising at least one tool for sizing, locating and implanting a reverse hip acetabular cup selected from:
   a drill guide handle;
   two or more than two drill bits;
   two or more than two drill guides;
   two or more than two second trial acetabular balls;
   a trial acetabular ball insertion-removal tool;
   two or more than two first trial acetabular balls;
   two or more than two trial acetabular cups;
   elements of an acetabular cup impactor assembly comprising another universal handle;
   an acetabular cup handle;
   an inner shaft having a knob at a proximal end thereof;
   two anteversion guide rods;
   a collet; and
   an acetabular ball impactor.

6. The surgical tray apparatus of claim 1, wherein the trial acetabular cups comprise through openings.

7. A surgical method comprising the use of the tools and trial implants from the surgical trays and components of claim 1 comprising:
   preparing a femur with the tools for preparation of a femur and preparing an acetabulum with the tools for preparing an acetabulum;
   placing the trial acetabular cup and trial acetabular ball in the acetabulum and when required, repeating this process until proper sizing of the implants is identified; and
   subsequently, removing the trial implants and implanting the properly sized permanent implants.

8. The method of claim 7 wherein a drill guide is used to drill the acetabulum so to accommodate screws to affix a permanent acetabular cup to the acetabulum.

9. A surgical tray apparatus and components according to claim 1 which at least one of:
   a press, a femoral cup locator and a plunger for pressing a polymer liner into a femoral cup.

10. The surgical tray apparatus and components of claim 1, further comprising at least one tool selected from:
    a reamer having a distal end for insertion into a femur and a proximal end;
    a right handed handle and a left handed handle configured for connection to the proximal end of the reamer;
    a T-handle configured for connection to the proximal end of the reamer;
    a box osteotome;
    two or more than two broaches each being sized to make a correspondingly sized opening in the femur;
    a hammer for pounding a broach into the femur; and
    a handle having a threaded portion configured to be threaded into a proximal end of a femoral implant.

11. The surgical tray apparatus and components of claim 1, further comprising at least one tool selected from:
    two or more than two different sized acetabular bone cutters;
    a drive shaft having a distal end configured for connection to a bone cutter;
    a drive shaft handle configured for connection to a proximal end of the drive shaft.

12. The surgical tray apparatus and components of claim 1, comprising:
    a trial acetabular ball insertion-removal tool.

13. The surgical tray apparatus of claim 1 wherein, a part of the trial femoral cup may be positioned within a space between the trial acetabular ball removably engaged on the stem of a trial acetabular cup and the inner concave surface of the trial acetabular cup.

14. A surgical tray apparatus and components thereof configured for use in hip replacement surgery comprising:
    trial implants for sizing, locating and implanting a reverse hip acetabular cup including at least two differently sized trial acetabular cups each having a hemispherical outer surface and an inner concave surface, optionally one or more through openings extending through the trial acetabular cups, the inner concave surface having an internally threaded stem, the stem having a height and extending from the inner concave surface and extending to an end having an opening, and at least two differently sized first trial acetabular balls each having a threaded portion removably engageable via mating threads within the internally threaded stem of a trial acetabular cup such that when fully engaged a part of the trial acetabular ball abuts the end of the stem, and an opening centered in a flattened portion of the trial acetabular ball opposite to the threaded portion, the opening being sized and shaped to receive a tool for tightening and loosening the trial acetabular ball when the threaded portion is engaged with the mating threads of the stem of a trial acetabular cup,
    and optionally,
    two or more than two trial femoral cups configured to be temporarily affixed to the proximal end of a broach or a femoral implant engageable with at least one of the first trial acetabular balls, each of the trial femoral cups having a base portion and a concave portion configured to articulate on a trial acetabular ball engaged with the stem of a trial acetabular cup;
    and/or
    at least one further article selected from: at least one tool, a press, a femoral cup locator and a plunger for pressing a polymer liner into a femoral cup.

15. The surgical tray apparatus and components of claim 14, comprising:
    a trial acetabular ball insertion-removal tool.

* * * * *